(12) United States Patent
Azuma et al.

(10) Patent No.: US 8,083,679 B1
(45) Date of Patent: Dec. 27, 2011

(54) ULTRASONIC IMAGING APPARATUS

(75) Inventors: Takashi Azuma, Kawasaki (JP);
Shinichiro Umemura, Muko (JP); Yo Taniguchi, Kokubunji (JP)

(73) Assignee: Hitachi Medical Corporation, Tokyo (JP)

( * ) Notice: Subject to any disclaimer, the term of this patent is extended or adjusted under 35 U.S.C. 154(b) by 1002 days.

(21) Appl. No.: 11/572,322

(22) PCT Filed: Jul. 20, 2005

(86) PCT No.: PCT/JP2005/013281
§ 371 (c)(1),
(2), (4) Date: Dec. 26, 2007

(87) PCT Pub. No.: WO2006/027899
PCT Pub. Date: Mar. 16, 2006

(30) Foreign Application Priority Data

Sep. 3, 2004 (JP) ................................. 2004-256448

(51) Int. Cl.
A61B 8/14 (2006.01)
(52) U.S. Cl. .......................... 600/443; 600/456; 600/455
(58) Field of Classification Search .................. 600/407, 600/441, 454, 453–457, 450, 443, 449, 459, 600/447, 458
See application file for complete search history.

(56) References Cited

U.S. PATENT DOCUMENTS

| | | | | |
|---|---|---|---|---|
| 5,860,927 A * | 1/1999 | Sakaguchi et al. | ............ | 600/453 |
| 5,899,861 A * | 5/1999 | Friemel et al. | ................ | 600/443 |
| 6,102,865 A * | 8/2000 | Hossack et al. | ............... | 600/459 |
| 6,110,114 A * | 8/2000 | Nock et al. | ..................... | 600/443 |
| 6,179,781 B1 * | 1/2001 | Phillips | ......................... | 600/454 |
| 6,210,334 B1 * | 4/2001 | Phillips | ......................... | 600/453 |
| 6,213,947 B1 * | 4/2001 | Phillips | ......................... | 600/443 |
| 6,464,637 B1 * | 10/2002 | Criton et al. | ................... | 600/441 |
| 7,128,713 B2 * | 10/2006 | Moehring et al. | ............. | 600/453 |
| 2003/0083578 A1 * | 5/2003 | Abe et al. | ...................... | 600/447 |
| 2003/0100832 A1 * | 5/2003 | Criton et al. | ................... | 600/443 |
| 2003/0158483 A1 * | 8/2003 | Jackson et al. | ................ | 600/449 |
| 2005/0085729 A1 * | 4/2005 | Abe | .............................. | 600/450 |
| 2007/0078326 A1 * | 4/2007 | Yoshikawa et al. | ........... | 600/407 |

FOREIGN PATENT DOCUMENTS

| | | |
|---|---|---|
| JP | 07-146304 | 6/1995 |
| JP | 11-262489 | 9/1999 |
| JP | 2000-245733 | 9/2000 |
| JP | 2001-070303 | 3/2001 |
| JP | 2001-521404 | 11/2001 |

* cited by examiner

Primary Examiner — Long V. Le
Assistant Examiner — Lawrence Laryea
(74) Attorney, Agent, or Firm — Antonelli, Terry, Stout & Kraus, LLP.

(57) ABSTRACT

An ultrasonic image capturing apparatus is disclosed for transmitting ultrasonic pulses from an ultrasonic probe in which elements are arranged two-dimensionally to a subject, receiving the ultrasonic pulses reflected by the subject, and displaying a slice image of the subject. A vector Doppler processor detects motion of the subject along the direction of an aperture of a receiving beam former, and a displacement detector detects motion of a focus region in the subject based on a result of computation of the vector Doppler processor. A scanning plate setting section determines an image capturing region by using ultrasonic waves by the displacement detector.

4 Claims, 8 Drawing Sheets

DIASTOLE

SYSTOLE

DIASTOLE

SYSTOLE

ULTRASONIC IMAGING APPARATUS

TECHNICAL FIELD

The present invention relates to an ultrasonic image capturing technique for displaying a slice image of a subject by using an ultrasonic beam.

BACKGROUND ART

An ultrasonic diagnostic apparatus transmits an ultrasonic beam from an ultrasonic probe to a subject and, on the basis of a reception signal received from the subject, obtains information necessary for diagnosis. In particular, high image capturing speed of ultrasonic image capturing can be utilized for a region whose motion is fast like the heart in a living body more than other image capturing methods such as image capturing methods using X-ray CT, MRI, and the like.

A change in the thickness of cardiac muscle accompanying beating is an element useful for examining various diseases of the heart, and measurement of a change in the thickness of cardiac muscle on an ultrasonic slice image is conventionally widely performed (refer to, for example, Japanese Patent Application Laid-Open No. 2001-70303).

In the case where the condition of a patient having ischemic heart disease is worsened, a region in which the thickness of the cardiac muscle is reduced is determined as a lesion. When attention is paid to the change rate of the thickness of cardiac muscle accompanying beating, before a condition becomes serious to an extend that the thickness of the cardiac muscle is reduced, the lesion can be detected. It becomes also possible to grasp the condition of the disease, so that measurement of the thickness of the cardiac muscle is valuable from the clinical point of view.

DISCLOSURE OF THE INVENTION

Problems to be Solved by the Invention

The heart beat is about once per second, and it is known that a data acquisition rate of about $\frac{1}{20}$ second is necessary to follow the fastest heart beat. On the other hand, the image capture rate of an ultrasonic slice image is about $\frac{1}{50}$ second, so that it can follow the speed of the heart beat.

In reality, however, the heart moves three-dimensionally. For ultrasonic three-dimensional image capturing, mechanical scanning for mechanically scanning a one-dimensional transducer array in an array direction and a direction orthogonal to the array direction or electronic scanning using a two-dimensional transducer array can be used. In any case, to maintain the image spatial resolution which is about the same as that of a slice image, since the resolution is obtained by multiplying image capture time of slice images by the number of images, time in the units of seconds is necessary, and images following the motion of the heart cannot be obtained.

FIG. 1 shows the relation between deformation accompanying beating of the heart and an ultrasonic image capture plane (slice plane). As shown in FIG. 1, a region B of interest (in this example, a lesion such as a cardiac infarction aura region) observed on an image A shifts according to the phase of cardiac muscle during beating in diastole and that in systole. In the case of cardiac muscle, to efficiently send blood from the ventricles and atriums, the cardiac muscle twists as if a towel is twisted. As a result, trace of changes in thickness becomes inaccurate.

An example in which a problem occurs in thickness measurement is clearly understood by comparison between FIGS. 4 and 5. FIG. 4 shows a slice image (schematic diagram) of cardiac muscle during diastole, and a hatched portion indicates the cardiac muscle. In the diagram, for convenience of explanation, X and Y show representative points (black points) placed in the cardiac muscle and the heart chamber. The distance between X and Y is measured as the thickness of the heart muscle in diastole. FIG. 5 shows a slice image (schematic diagram) of cardiac muscle during systole, and a hatched portion indicates the cardiac muscle. X and Y shown in FIG. 5 indicate results of trace of the representative points X and Y by interframe correlation on the basis of FIG. 4. Boundary points are obtained as X and Y' on the basis of FIG. 5. It is understood from the result that the points X and Y' as a result of trace of the representative points in diastole and apparent boundary positions X and Y on an image are deviated from each other. Consequently, the distance between X and Y is determined as thickness in the cardiac muscle in systole.

The reason is considered that since the object described with reference to FIG. 1 deviates from the image capture plane (slice plane) B, images of the peripheral images overlap the cross sections. When the thickness of the cardiac muscle is obtained from the apparent slice plane, there is the possibility that an accurate change in the thickness of the cardiac muscle cannot be obtained correctly.

An object of the present invention is to provide an ultrasonic image capturing apparatus capable of tracing a section of an object and forming an image also in the case where the object moves and deviates from an image capture section.

Means for Solving the Problems

To achieve the object, an ultrasonic image capturing apparatus of the invention as the following features.

(1) An ultrasonic image capturing apparatus for transmitting ultrasonic pulses from an ultrasonic probe to a subject, receiving the ultrasonic pulses reflected by the subject, and capturing a slice image of the subject, including means for detecting a motion of a region of interest in the subject on the basis of a reception signal received from the subject, wherein a slice image of the subject is captured on the basis of an image plane corrected by tracing the detected motion of the region of interest in the subject.

In the configuration, the detecting means detects a motion of the region of interest in the subject by the vector doppler method. The ultrasonic image capturing apparatus has a slice image capturing mode for capturing a slice image of the subject and a displacement detection mode for detecting a motion of a region of interest in the subject, and further includes means for switching between the slice image capturing mode and the displacement detection mode.

(2) An ultrasonic image capturing apparatus for transmitting ultrasonic pulses from an ultrasonic probe in which elements are arranged two-dimensionally to a subject, receiving the ultrasonic pulses reflected by the subject, and capturing a slice image of the subject, including: a transmission beam former for forming a transmission ultrasonic beam from the ultrasonic pulses; a receiving beam former for forming a reception ultrasonic beam from the received ultrasonic pulses; a vector doppler processor for detecting a motion of the subject along the direction of an aperture of the receiving beam former on the basis of an output result of the receiving beam former by the vector doppler method; a displacement detector for obtaining a motion vector of a region of interest in the subject on the basis of a computation result of the vector doppler processor; a scanning plane setting section for determining an image capture region with ultrasonic waves on the basis of a motion vector of the subject; an envelope detector for performing detection from an output result of the receiving beam former; a scan converter for forming an image of a result of the envelope detector; and a display for displaying an output of the scan converter, wherein the transmission beam former transmits a beam to a transmission beam point on a scanning plane set by the scanning plane setting section, and the receiving beam former is set so as to make a focus on a point on the scanning plane set by the scanning plane setting section.

In the configuration, the apparatus has a slice image capturing mode for capturing an image of the subject and a displacement detection mode for detecting a motion of a region of interest in the subject, and further comprises a displacement detection/imaging selector for switching between the slice image capturing mode and the displacement detection mode.

According to the present invention, an ultrasonic image capturing apparatus capable of forming an image while always tracing a section of a region of interest in an object which is complicatedly deformed on a three-dimensional space at high speed can be realized.

BEST MODE FOR CARRYING OUT THE INVENTION

An embodiment of the present invention will be described in detail hereinbelow with reference to the drawings.

Figure 1:
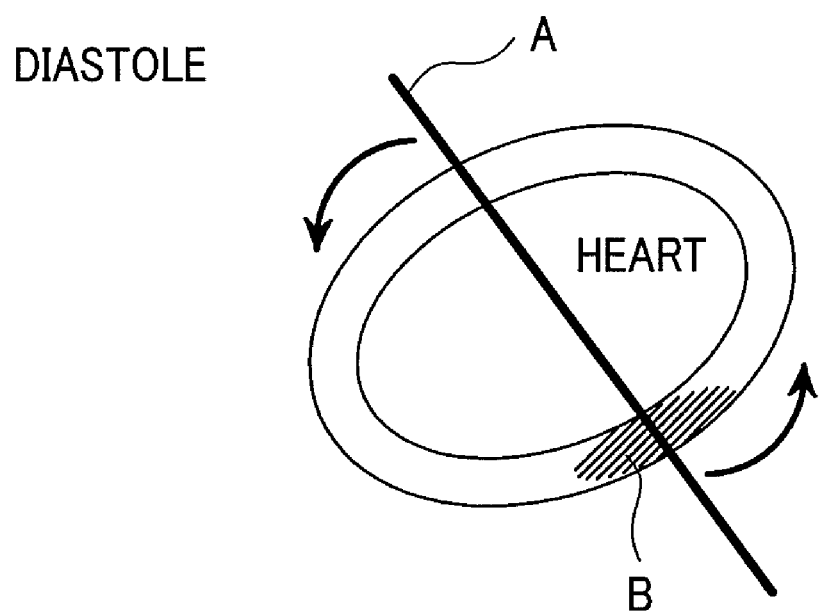
FIG. 1 is a diagram showing the relation between a deformation accompanying heart beating and an ultrasonic image capture plane in a conventional technique.
Figure 1:
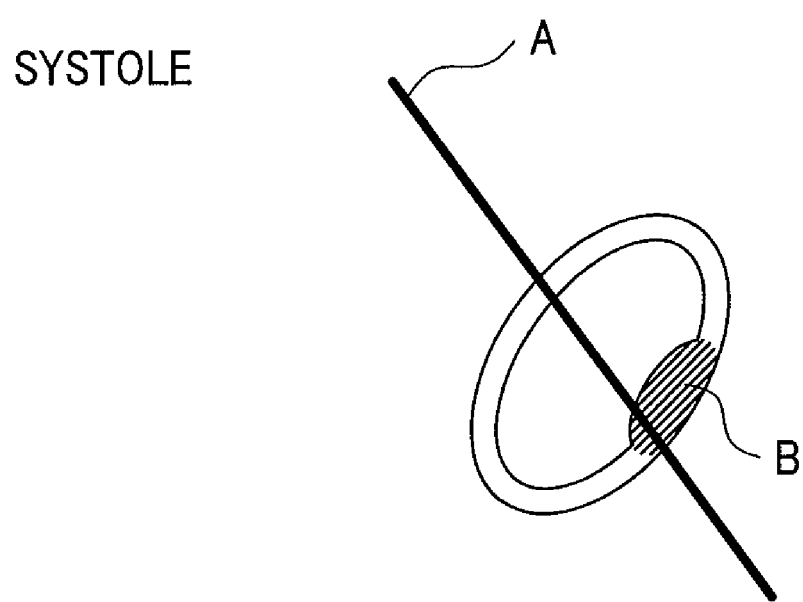
Figure 2:
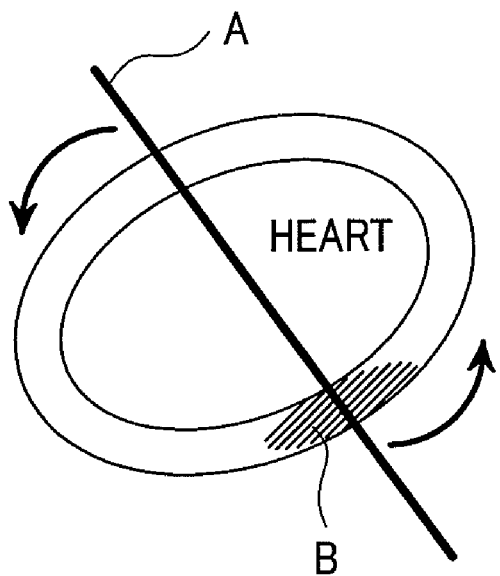
FIG. 2 is a diagram showing the relation between a deformation accompanying heart beating and an ultrasonic image capture plane in the present invention.
Figure 2:
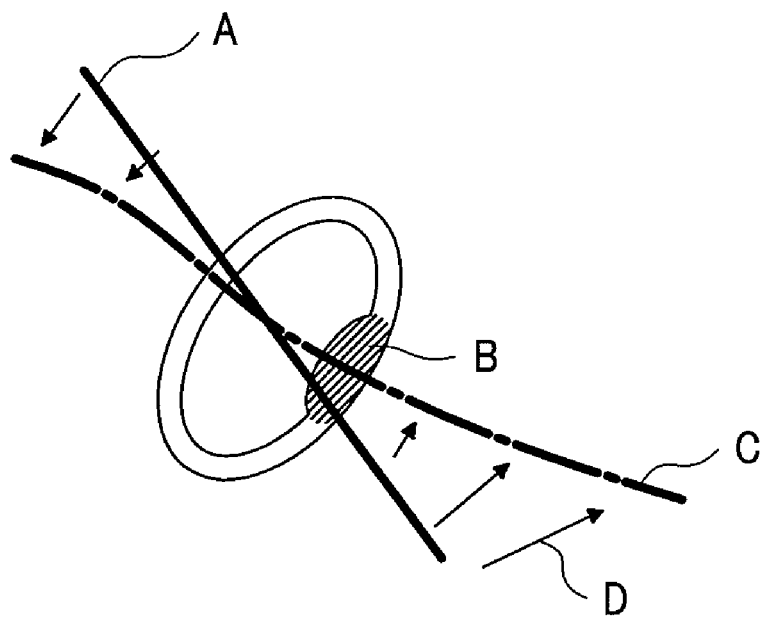
Figure 3:
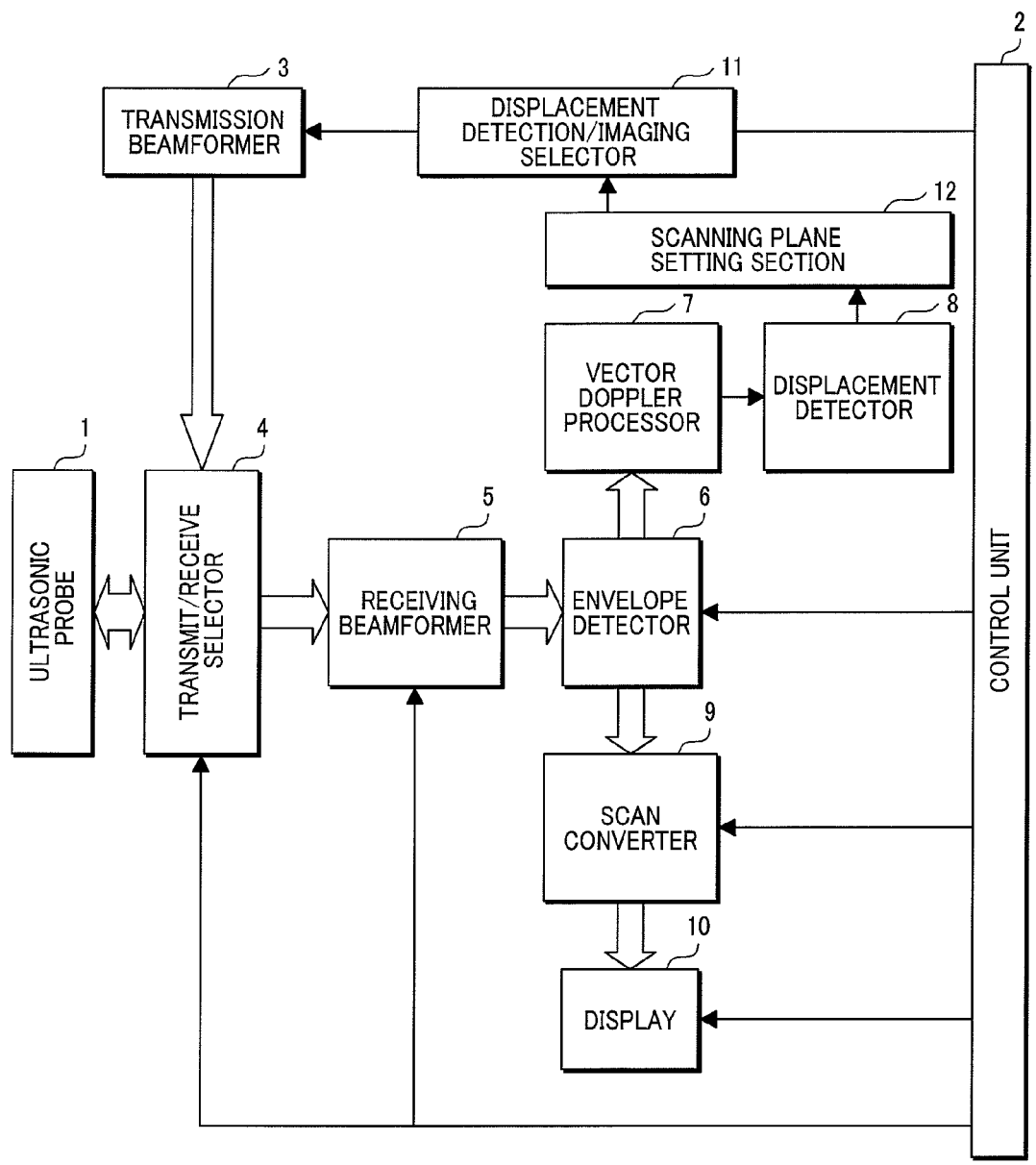
FIG. 3 is a diagram showing a configuration example of an ultrasonic image capturing apparatus as an embodiment of the invention.

FIG. 3 shows a configuration example of an ultrasonic image capturing apparatus as an embodiment of the invention. The apparatus has a control unit 2, an ultrasonic probe 1 in which elements are arranged two-dimensionally, a transmit/receive selector 4 connected to the ultrasonic probe 1 and capable of transmitting a signal to an arbitrary element and receiving a signal from an arbitrary element, a transmission beam former 3 connected to the transmit/receive selector 4 and transmitting ultrasonic waves to a predetermined position in a subject (not shown), a receiving beam former 5 connected to the transmit/receive selector 4 and selectively amplifying a reception signal from the predetermined position in the subject, an envelope detector 6 for detecting an envelope component from an output of the receiving beam former 5, and a scan converter 9 for displaying output of the envelope detector 6 on a display 10. In the invention, a two-dimensional ultrasonic probe is used. Due to restriction of image capturing speed, a two-dimensional slice image is displayed on the display 10. An initial two-dimensional slice image is set so as to be a plane including the region B of interest as shown by the slice image A in FIG. 2 which will be described later in the transmission beam former 3 and the receiving beam former 5.

The invention is directed to trace the position in a slice plane formed by focal points of the transmission beam former 3 and the receiving beam former 5 in accordance with a deformation of a subject. For the purpose, particularly in the invention, in addition to a normal slice image capturing mode for capturing a slice image of the subject, a displacement detection mode for detecting the motion (displacement) of a subject is provided. The displacement detection mode and the slice image capturing mode can be switched by a displacement detection/imaging selector 11. In the following, a line connecting an ultrasonic transmission direction and the center of a transmit/receive aperture will be called a raster. In the slice image capturing mode, ultrasonic waves are transmitted in the raster direction. An echo signal of the ultrasonic wave from above the raster is measured by the dynamic focus method. An intensity direction in the depth direction on the raster is converted to brightness, and the raster is scanned on a predetermined cross section, thereby obtaining a slice image.

Figure 6:
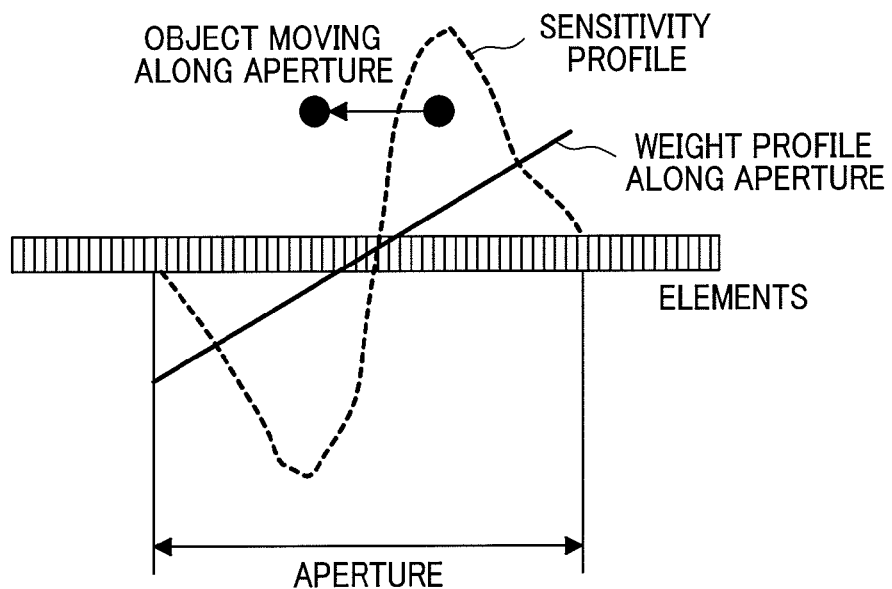
FIG. 6 is a diagram showing application of the vector Doppler method in the present invention.

In contrast, in the displacement detection mode, the known vector doppler method (reference document: Japanese Patent Laid-Open No. H7-146304) is used. The simplest vector doppler method can be realized by, as shown in FIG. 6, the signs of weights on reception signals in elements at both ends of the aperture of the receiving beam former 5 are made opposite to each other (positive and negative signs), so that a receiving beam having a sensitivity profile in the aperture direction can be obtained. When there is a sensitivity profile in the direction parallel with the aperture as described above, a receiving beam has sensitivity to a lateral movement (in the aperture direction) of the object. With respect to the aperture shown in FIG. 6, first, an aperture for vector doppler measurement is defined in the direction perpendicular to an image capturing face in the image capturing mode on the two-dimensional array, and motion of a subject in the direction along the aperture is detected. The vector doppler computation is performed by a vector doppler processor 7. On the basis of a result of the vector doppler processor 7, a motion (displacement) vector of the subject is obtained by a displacement detector 8. According to the obtained motion vector of the subject, the raster position in the image capturing mode is corrected by a scanning face setting section 12. On the basis of the correction result of the raster position, a transmission wave focus position and a reception wave focus position are corrected, and a slice image is captured.

FIG. 2 shows the relation between a deformation accompanying heart beating and an ultrasonic image capture plane (slice plane) in the present invention. By repeating the displacement detection mode in the image capturing mode, as shown in FIG. 2, the position of the image capture plane (slice) A is corrected on the basis of a displacement vector D detected by the vector doppler method, and the position of a new image capture plane C following the motion of the subject is obtained. Specifically, in diastole, even when the region B of interest (in the example, lesion part such as cardiac infarction aura region) observed in the image capture plane A shifts in systole, by the new image capture plane C obtained by tracing the movement and correcting the position, an image of a section of the target region can be captured.

Figure 4:
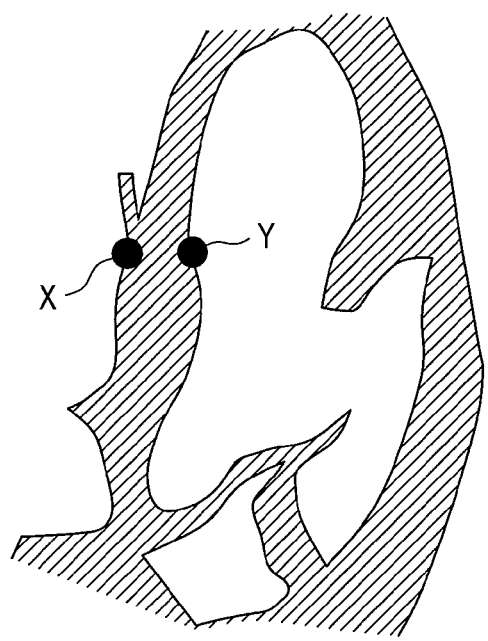
FIG. 4 is a diagram showing an example of a section of cardiac muscle.
Figure 5:
FIG. 5 is a diagram showing a section of cardiac muscle and a result of trace of a boundary point.
Figure 7:
FIG. 7 is a diagram showing effects in the case of using the present invention.

From the result, a change with time in thickness of cardiac muscle on a slice plane described above can be accurately measured. FIG. 7 is a diagram for explaining an effect of the case where the present invention is used. The diastole is based on the same data as that shown in FIG. 4, and FIG. 7 shows a result of tracing a slice plane in systole. By tracing the position of the slice plane, the position of Y is displayed on the boundary of the cardiac muscle. Accurate thickness of the cardiac muscle is reflected in the distance between X and Y.

Next, as another embodiment of the invention, an example of tracing a slice plane with motion of the subject by using the above-described method, thereby enabling a strain imaging to be captured will be described.

In a strain imaging, RF data in the regions of interest between frames is correlated, and an average moving amount in each of the regions of interest is calculated. In the interframe correlation, when the region of interest is off from the slice plane, correlation cannot be obtained and a moving amount, that is, a deformation amount cannot be known. When the method of the invention is employed, the region of interest can be always traced. Thus, also in the case where motion is very large or fast like cardiac muscle, the region of interest can be captured without deviation from the slice plane. In known strain imaging capturing, pressure is applied from the outside and a deformation under pressurization is monitored, thereby imaging hardness. In the case of the heart, the cardiac muscle operates spontaneously without pressurization. Therefore, by just correlating data, a strain imaging, that is, a parameter related to modulus of elasticity can be measured.

Further, the present invention can be also applied to a cardiac muscle contrast imaging. The cardiac muscle contrast imaging is a diagnostic method of parenterally administering a contrast agent, and examining the picture of the contrast agent in the regions of the heart muscle, thereby detecting an ischemic region in the cardiac muscle. Since attenuation varies depending on paths of sound, even if intensity is simply compared within an image, quantitative comparison of the degree of penetration of the contrast agent cannot be made. On the other hand, a method of expressing intensity I as I=Ap($-\alpha$t) and examining $\alpha$, thereby determining ischemia is proposed. By the equation, variations in attenuation according to sound paths are included in a coefficient A, and no influence is exerted on $\alpha$. If an observation region shifts at the time of estimating an intensity change rate as described above in the specification, a large error occurs in estimation of $\alpha$. A method of adjusting an image capture region in accordance with a motion of an object according to the present invention is a method of substantially solving the problem.

In any of the foregoing embodiments, by switching between the slice image capturing mode and the displacement detecting mode, the signal acquisition rate in the slice image capturing mode is reduced to the half. In the case of performing three-dimensional image capturing, the signal acquisition rate is lowered by the amount corresponding to the number of frames in the elevation axis direction, typically, 50 to 100 frames. Consequently, as compared with the three-dimensional image capturing, the data acquisition rate in the method of the present invention is higher by about 25 to 50 times. In particular, in the case where beating of the heart is a target, three-dimensional image capturing cannot trace the target. However, in the method of the present invention, the frame rate of about 25 can be assured, so that the method can sufficiently trace the target.

Although the case where the displacement varies in the depth direction has not been described, in this case, there may be methods of using an average value, obtaining an average with weight of intensity of a signal, increasing the weight toward the region of interest, and the like. A transmission multistage focus can be also performed by preparing some displacement detection regions in the depth direction and setting a plurality of image capture positions in the depth direction.

The number of detection points in one frame of the displacement detector is as follows. In the case of an ultrasonic slice image, when the width of point response function is larger than the inverse number of the highest frequency of a distribution pattern of a reflector, the larger the number of sampling points in the aperture direction is, the larger the information amount is. However, on detection of a displacement, deformation of the object is smooth and may be approximated by a high-order function of the first or second degree as shown by C in FIG. 2. Consequently, it is unnecessary to finely sample the deformation as compared with the case of capturing a slice image. The number of sampling points is reduced, a displacement is detected, and the reduced points are reconstructed by interpolation, thereby enabling drop in image capturing speed to be suppressed to the minimum.

Figure 8:
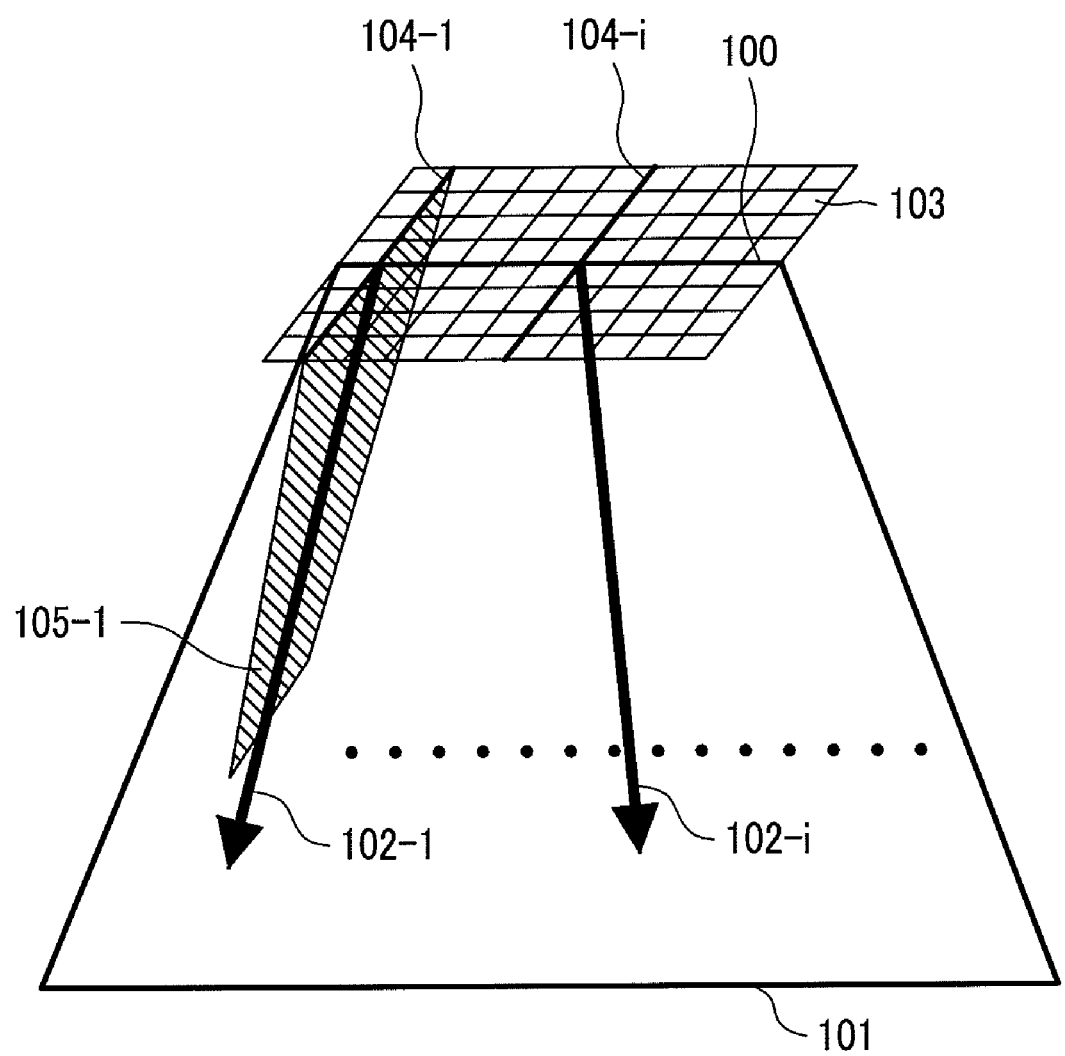
FIG. 8 is a diagram showing the relations among a probe, an image capture plane, and a displacement detection plane in the case of using the present invention.
Figure 9:
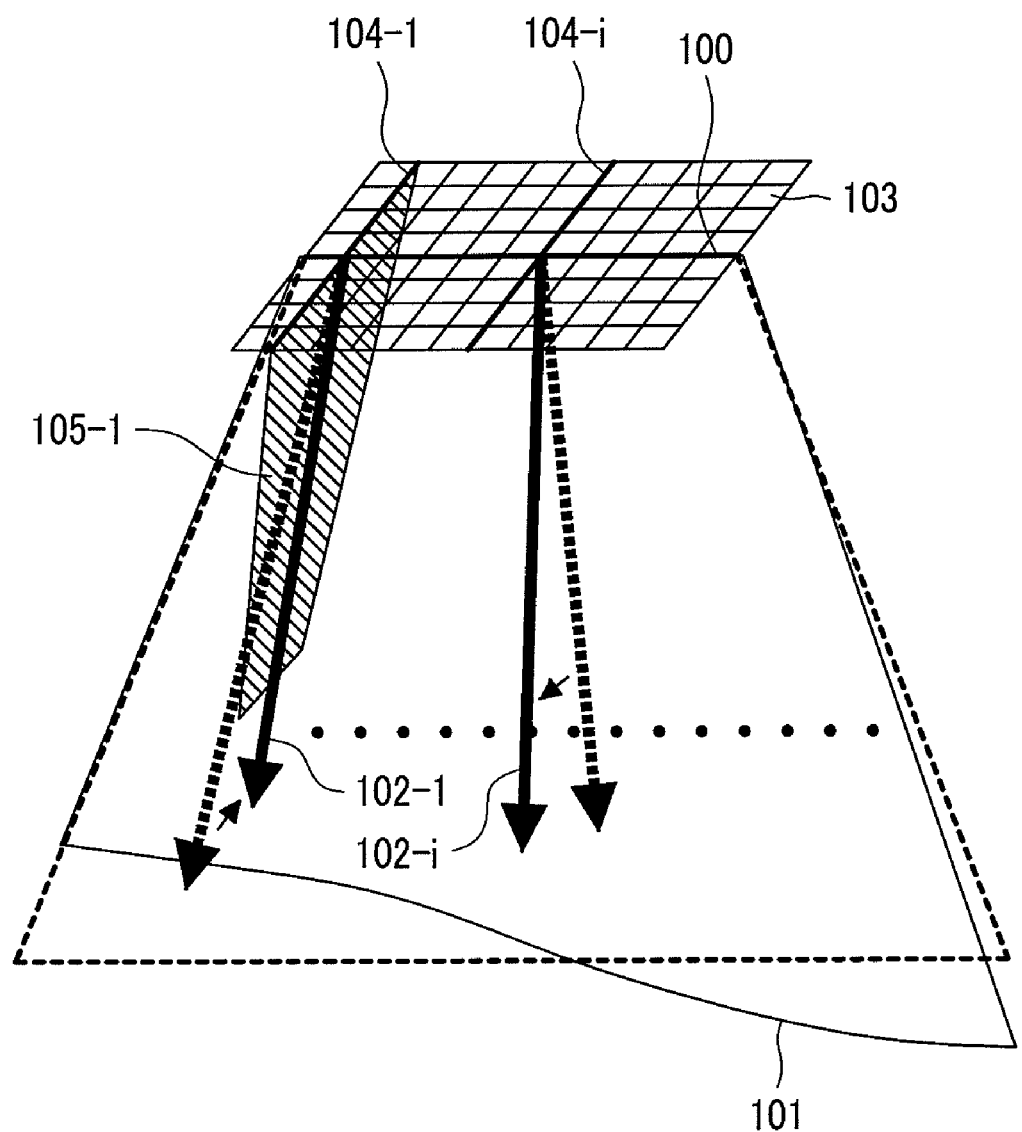
FIG. 9 is a diagram showing the relations among a probe, an image capture plane, and a displacement detection plane in the case of using the present invention.

FIG. 8 shows the spatial relations among a probe, an image capture plane, and the displacement detection direction. An example of using a sector-type probe will be described. An image capture plane 101 is captured by using an image capture aperture 100. For each of a plurality of rasters 102 in the image capture plane 101, a displacement detection aperture 104 is defined in a direction orthogonal to an image capture plane on a probe surface 103. By using the displacement detection apertures 104, an image capture plane 105 orthogonal to both the image capture plane and the probe surface is formed. The image capture plane 101 is constructed by the plurality of rasters. For example, when the number of rasters is "n", the rasters are 102-1 to 102-n. In correspondence with the rasters, the displacement detection apertures 104 are displacement detection apertures 104-1 to 104-n. By estimating movement of an object in the direction orthogonal to the image capture plane 101 in the image capture plane 105 for displacement detection, the raster position is corrected in the following frame. Therefore, a movement of the target can be followed. As a sequence, waves are first transmitted/received to/from the rasters 102-1, 102-2, . . . , 102-i, and 102-n by using the image capture apertures 100. Subsequently, by using the apertures 104-1, 104-2, . . . , 104-i, . . . , and 104-n, components orthogonal to the image capture plane 101 in the movement of the object corresponding to the rasters are estimated. Image capture of one frame is completed. The next frame is captured by correcting the raster positions in accordance with the motion amount estimated at the time of capturing the first frame as shown in FIG. 9. By repeating the operation, image capturing in a plane always tracing a motion can be performed. As already described above, it is unnecessary to make the displacement detection apertures 104 correspond to all of the rasters. The rasters can be reduced spatially in such a manner that one displacement detection aperture 104 is defined for a plurality of rasters and a displacement between the rasters is estimated by interpolation. Reduction with time is also possible in such a manner that displacement estimation is performed every some frames without detecting a displacement every frame. By any of the reducing operations, the frame rate of an image improves. After the displacement is estimated, the movement amount among the frames is calculated by "displacement speed×frame rate". When the movement amount is smaller than the slice thickness, displacement detection is reduced with respect to time. When the displacement does not fluctuate among neighboring rasters, a method of spatially reducing the displacement detection can be selected.

Figure 10:
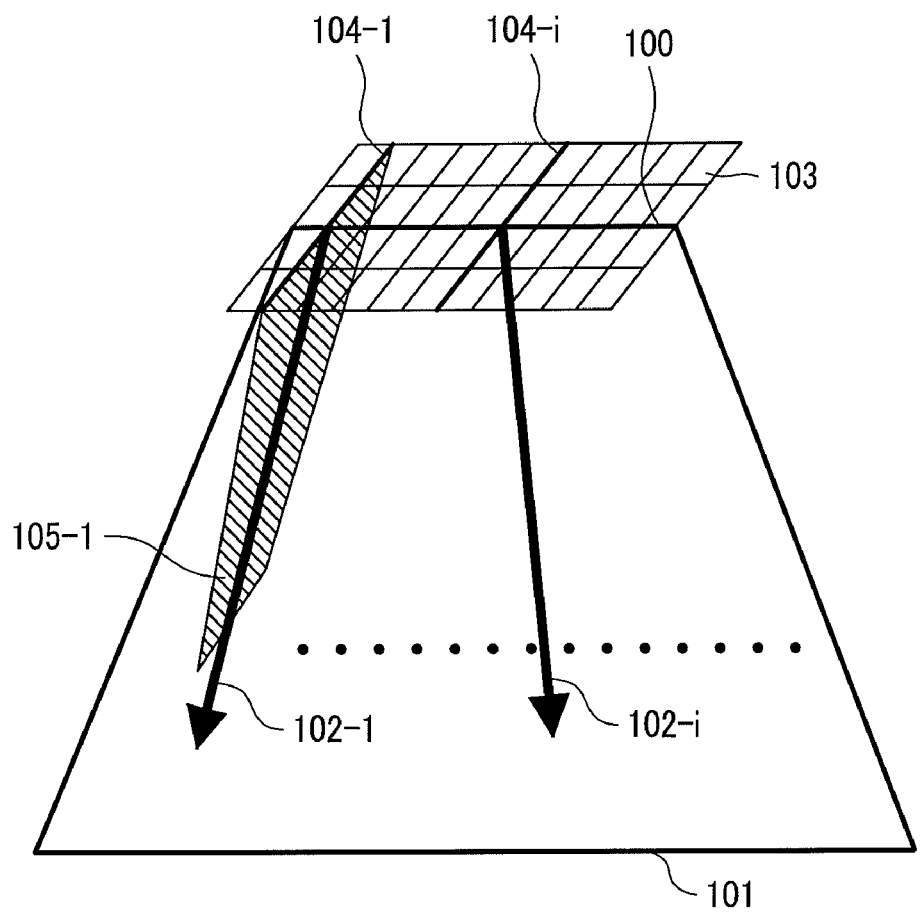
FIG. 10 is a diagram showing the relations among a probe, an image capture plane, and a displacement detection plane in the case of using the present invention.

The invention has been described by the example using the isotropic two-dimensional probe. However, the image capture plane is limited in one direction with respect to a probe. The number of elements in the probe and the intervals between the elements in a direction along the image capture plane may be different from those in a direction orthogonal to the direction. FIG. 10 shows a configuration example in which the element interval in the direction orthogonal to the image capture plane is longer than that in the direction along the image capture plane. Different from a configuration so-called a 1.5-dimensional array in which only focus in the elevation axis is switched, the beam deflection direction has to be also tilted. Consequently, the element interval has to be set finer than that in the 1.5-dimensional array. In any case, by making the element interval in one of the axes longer than that in the two-dimensional array for obtaining a normal three-dimensional volume image, the apparatus can be simplified.

INDUSTRIAL APPLICABILITY

As described in detail above, according to the present invention, an ultrasonic image capturing apparatus capable of forming an image while always tracing a section of a region of interest in an object which is complicatedly deformed on a three-dimensional space at high speed can be realized. Thus, a change with time in the thickness of a region of interest and a change with time in the modulus of elasticity of a region of interest can be measured accurately. The present invention can be used in the medical field.

The invention claimed is:

1. An ultrasonic image capturing apparatus for transmitting ultrasonic pulses from an ultrasonic probe in which elements are arranged two-dimensionally to a subject, receiving the ultrasonic pulses reflected by the subject, and capturing a slice image of the subject, comprising:

a transmission beam former for forming a transmission ultrasonic beam from the ultrasonic pulses;

a receiving beam former for forming a reception ultrasonic beam from the received ultrasonic pulses;

a vector Doppler processor for detecting a motion of the subject along an aperture direction of the receiving beam former on the basis of an output result of the receiving beam former by a vector Doppler method;

a displacement detector for obtaining a motion vector of a region of interest in the subject on the basis of a computation result of the vector Doppler processor;

a scanning plane setting section for determining an image capture plane with ultrasonic waves on the basis of a motion vector of the subject;

an envelope detector for performing detection from an output result of the receiving beam former;

a scan converter for forming an image of a result of the envelope detector; and a display for displaying an output of the scan converter, wherein the transmission beam former transmits a beam to a transmission beam point on a scanning plane set by the scanning plane setting section, and the receiving beam former is set so as to make a focus on a point on the scanning plane set by the scanning plane setting section.

2. The ultrasonic image capturing apparatus according to claim 1, wherein the apparatus has a slice image capturing mode for capturing an image of the subject and a displacement detection mode for detecting a motion of a region of interest in the subject, and further comprises a displacement detection/imaging selector for switching between the slice image capturing mode and the displacement detection mode.

3. The ultrasonic image capturing apparatus according to claim 1, wherein the aperture direction is orthogonal to the scanning plane.

4. The ultrasonic image capturing apparatus according to claim 1, wherein a number of raster scans in the aperture direction of the receiving beams former is reduced spatially or with time in the displacement detection mode.

* * * * *